United States Patent [19]

Takago et al.

[11] Patent Number: 5,247,101
[45] Date of Patent: Sep. 21, 1993

[54] CYCLIC PERFLUOROKETONES AND METHOD OF MAKING

[75] Inventors: Toshio Takago, Annaka; Yasuo Tarumi; Kouichi Yamaguchi, both of Takasaki, all of Japan

[73] Assignee: Shin-Etsu Chemical Co., Ltd., Tokyo, Japan

[21] Appl. No.: 868,769

[22] Filed: Apr. 16, 1992

[30] Foreign Application Priority Data

Apr. 16, 1991 [JP] Japan ............................ 3-111099

[51] Int. Cl.$^5$ ............................................ C07D 323/00
[52] U.S. Cl. ..................................... 549/347; 549/352
[58] Field of Search ............................. 549/347, 352

[56] References Cited

U.S. PATENT DOCUMENTS

| | | | |
|---|---|---|---|
| 3,250,807 | 5/1966 | Fritz et al. ........................ | 260/535 |
| 4,067,884 | 1/1978 | Martini ............................ | 260/340.6 |
| 4,136,121 | 1/1979 | Martini et al. ................... | 260/593 H |
| 4,593,110 | 6/1986 | Goldwasser et al. ............. | 549/347 |
| 5,120,459 | 6/1992 | Kalota et al. .................... | 549/347 |

FOREIGN PATENT DOCUMENTS 52-10209  1/1977  Japan ................................. 549/347

OTHER PUBLICATIONS

Japanese Abstract Kokai No. 52-10209, Publication Date: Jan. 26, 1977.

*Primary Examiner*—C. Warren Ivy
*Assistant Examiner*—Raymond Covington
*Attorney, Agent, or Firm*—Millen, White, Zelano & Branigan

[57] ABSTRACT

Provided are novel cyclic perfluoroketones which are thermally and chemically stable fluids. They are prepared by reacting perfluorodicarboxylic acid difluorides with carbonates in aprotic polar solvents.

10 Claims, No Drawings

CYCLIC PERFLUOROKETONES AND METHOD OF MAKING

This invention relates to novel cyclic perfluoroketones and a method for making the same.

BACKGROUND OF THE INVENTION

U.S. Pat. No. 4,067,884 assigned to Hoechst discloses perfluoroketones of formula (3):

wherein $R^1$ and $R^2$ are independently perfluoroalkyl groups, which may contain at least one oxygen atom as an ether bond, $R^1$ and $R^2$, taken together, have 10 to 80 carbon atoms, and $R^1$ and $R^2$ may be linear, branched or cyclic. The perfluoroketones are neutral liquids which are stable against acids and oxidizing agents and useful as heat transfer media when they are of low molecular weight and as lubricants when they are of high molecular weight.

These perfluoroketones, however, have a boiling point as high as about 100° to 500° C. which limits their use. There is a need for perfluoroketones having a lower boiling point or unique properties so that they may find a wider variety of applications.

SUMMARY OF THE INVENTION

Therefore, an object of the present invention is to provide novel cyclic perfluoroketones. Another object of the present invention is to provide a method for synthesizing cyclic perfluoroketones.

The inventors have found that by reacting a perfluorodicarboxylic acid difluoride of formula (2) with a carbonate salt in an aprotic polar solvent, the acid fluorides at both ends are condensed into cyclic form through mild ionic reaction to form a novel cyclic perfluoroketone of formula (1).

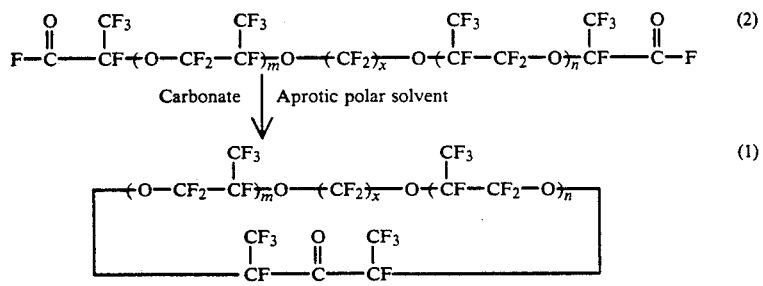

In the formulae, x is an integer of from 2 to 10, and m and n each are an integer of from 0 to 2.

The cyclic perfluoroketones of formula (1) are thermally and chemically very stable liquids and useful as reaction solvents in the chemical industry, heat transfer media, leak test fluids in the semiconductor industry, inert liquids for vapor phase soldering, and dielectric fluids in electric equipment. In particular, the cyclic perfluoroketone of formula (1) wherein both m and n are equal to 0 and x is equal to 2 has a lower boiling point of 84° C. and will thus find a wider variety of applications than the conventional perfluoroketones, shown in U.S. Pat. No. 4,067,884.

By utilizing the known photo decarbonylation as disclosed in Japanese Patent Application Kokai No. 10209/1977 by Hoechst, the cyclic perfluoroketones of formula (1) can be converted into cyclic perfluoroethers of formula (4) under moderate conditions in high yields according to the following scheme. The resulting cyclic perfluoroethers are more stable than the cyclic perfluoroketones and find use in the same applications as the cyclic perfluoroketones.

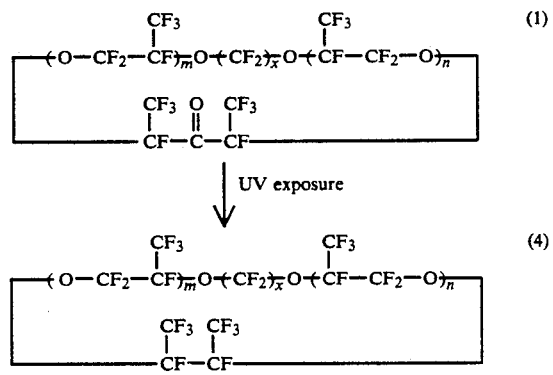

The cyclic perfluoroketones of formula (1) which have a carbonyl group are also used as precursors in synthesizing various compounds having a cyclic perfluoroether residue.

U.S. Pat. No. 4,136,121 assigned to Hoechst discloses to react $R^1CO_2M$ wherein $R^1$ is a perfluoroalkyl group having 2 to 50 carbon atoms which may contain at least one ether oxygen and M is a metal selected from the group consisting of Li, Na, K, Rb, Cs and Ag with $R^2COF$ wherein $R^2$ is a perfluoroalkyl group having 2 to 50 carbon atoms which may contain at least one ether oxygen in an aprotic polar solvent at a temperature of 20° to 200° C. for synthesizing a perfluoroketone $R^2COR^3$ wherein $R^3$ is $R^1$ or an isomer of $R^1$. Also disclosed is to react $R^1COF$ with $M_2CO_3$ to form $R^1CO_2M$ in situ which is further reacted with $R^1COF$ coexisting in system for synthesizing $R^3COR^3$ wherein $R^1$, M and $R^3$ are as defined above. This patent, however, does not refer to perfluoroketones having a cyclic structure in the backbone. The inventors first discovered the cyclic perfluoroketones of formula (1).

DETAILED DESCRIPTION OF THE INVENTION

The present invention provides novel cyclic perfluoroketones of formula (1).

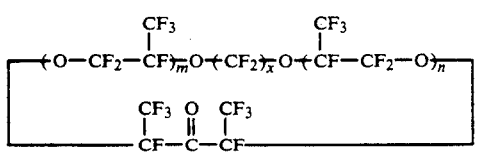

wherein x is an integer of from 2 to 10, and m and n are independently an integer of from 0 to 2. (The definition of x, m and n are the same hereinafter.) They can be prepared by reacting perfluorodicarboxylic acid difluorides with carbonate salts in an aprotic polar solvent.

The perfluorodicarboxylic acid difluorides used herein are represented by formula (2).

These perfluorodicarboxylic acid difluorides may be obtained by a well known technique (see U.S. Pat. No. 3,250,807) from a perfluorodicarboxylic acid difluoride free of an ether bond of the following formula (5) and hexafluoropropylene oxide of the following formula (6).

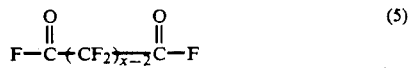

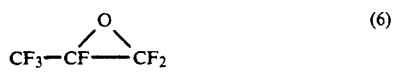

The carbonates used herein are represented by the general formula: $M_2CO_3$ wherein M is selected from the group consisting of Li, Na, K, Rb, Cs, and Ag, with $Na_2CO_3$ and $K_2CO_3$ being preferred. Use of anhydrous carbonate salts is preferred in order to control undesired side reaction. It is thus recommended to remove water from the carbonate salts by heating or vacuum drying prior to use.

The aprotic polar solvents used herein include amides such as dimethylformamide, dimethylacetamide, and hexamethylphosphoric triamide; and ethers such as diethyl ether, tetrahydrofuran, dioxane, ethylene glycol dimethyl ether (glyme), diethylene glycol dimethyl ether (diglyme), triethylene glycol dimethyl ether (triglyme), and tetraethylene glycol dimethyl ether (tetraglyme), with the diglyme, triglyme and tetraglyme being preferred. It is also recommended to remove water from the solvents prior to use.

Though not bound to the theory, it is believed that the conversion of the perfluorodicarboxylic acid difluorides of formula (2) into the cyclic perflurorketones of formula (1) proceeds through the process that the acid fluoride at one molecular end of the perfluorodicarboxylic acid difluoride first reacts with a carbonate to form a carboxylate which, in turn, reacts with the acid fluoride at the other end to form a cyclic ketone. This process is illustrated by the following chemical scheme.

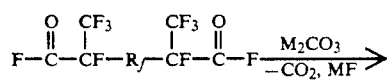

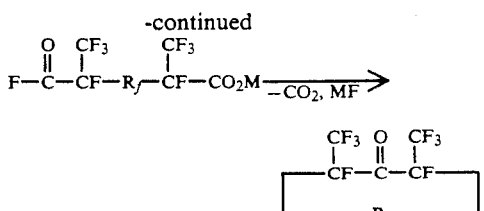

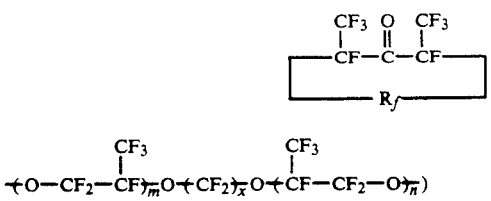

The molar ratio of the carbonate to the perfluorodicarboxylic acid difluoride used is 1:1 from a stoichiometric aspect, but it is preferable in practice to use the carbonate in excess for reaction efficiency. For better results, the carbonate and the perfluorodicarboxylic acid difluoride are used in a molar ratio of from 1.2/1 to 5.0/1. If the amount of the carbonate used exceeds this range, there is the risk that undesirably both the ends of the molecule become carboxylates. The amount of the solvent used is not critical although it is often used in an amount of about 0.2 to 20 liters per mole of the perfluorodicarboxylic acid difluoride.

Reaction may be effected by adding dropwise the perfluorodicarboxylic acid difluoride to a mixture of the carbonate and the solvent, preferably at a temperature of 20° to 200° C. At the end of addition, it is sometimes necessary to heat the reaction mixture to a temperature of 100° to 200° C. for increasing the conversion rate of the reactant, preferably to a temperature of 150° to 200° C. for optimum reaction rates. The progress of reaction can be monitored by infrared spectroscopy wherein the absorption of acid fluoride appearing near 1890 cm$^{-1}$ diminishes and eventually disappears. The reaction pressure is not critical and may be atmospheric or under pressure in an autoclave. Atmospheric pressure is convenient because reaction is accompanied by evolution of carbon dioxide gas. At the end of reaction, the product or cyclic perfluoroketone may be isolated by distillation. It is possible to sequentially distill out the product as it is produced during reaction.

EXAMPLE

Examples of the present invention are given below by way of illustration and not by way of limitation.

EXAMPLE

A 3-liter glass reactor equipped with a stirrer, a distillation head connected to a condenser and a cock for distilling out the product, a thermometer, and a heating bath was charged with 500 ml of dry diglyme and 424 grams (4 mol) of dry sodium carbonate. Reaction was conducted in a nitrogen gas stream by adding dropwise 426 grams (1 mol) of perfluoro-2,7-dimethyl-3,6-dioxasuberic acid difluoride of the following formula to the reactor at a temperature of 80° C. over one hour.

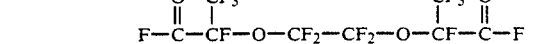

At the end of addition, the temperature was raised to 150° C. and the reactor was maintained at the temperature for 3 hours while allowing the product to distill out. The crude product was distilled under atmospheric pressure, yielding 171 grams (0.48 mol) of perfluoro-2,7-dimethyl-3,6-dioxacycloheptanone of the following formula (5) having a boiling point of 84° C. The following structure was established by the analytical data.

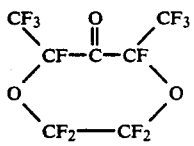

IR spectrum: 1790 cm$^{-1}$ $^{19}$F-NMR spectrum: The chemical shifts are relative to CF$_3$COOH. Two values were observed probably because two trifluoromethyl groups formed cis and trans isomers.

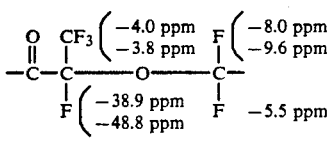

$^{13}$C-NMR spectrum: The chemical shifts are relative to TMS. Two values were observed for the same reason as above.

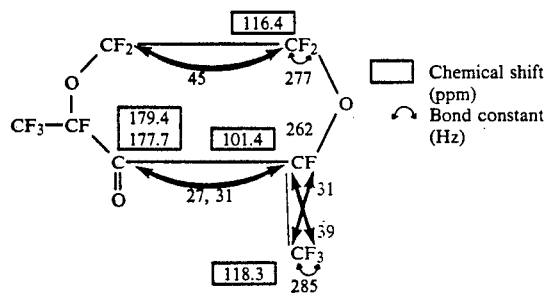

Mass spectrum: 341 (M—F)
263 CF$_3$—CF—O—CF$_2$—CF$_2$—O—CF
132 O—CF$_2$—CF$_2$—O
100 C$_2$F$_4$ Elemental analysis:
|   | Calcd. | Found |
|---|--------|-------|
| C: | 23.4% | 23.7% |
| F: | 63.3% | 62.5% |

REFERENCE EXAMPLE

A 100 ml glass reactor equipped with UVL-100HA high-pressure mercury lamp (manufactured by Riko Kagaku Sangyo K.K.) was charged with 175 grams (0.49 mol) of the perfluoro-2,7-dimethyl-3,6-dioxacycloheptanone obtained in Example. The reactor was also equipped with a dry ice condenser and a magnetic stirrer, and argon gas was slowly passed therethrough. After 190 hours of UV exposure, the disappearance of the reactant was observed by gas chromatography. There was obtained 146.5 grams (yield 81%) of a crude product having a purity of 89%. Distillation yielded 104.5 grams of a fraction having a boiling point of 65° C. with a purity of higher than 97%. This product was identified to be perfluoro-2,3-dimethyl-1,4-dioxane of the following formula (6) by the analytical data.

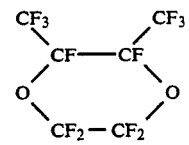

IR spectrum: No absorption appeared at wave numbers higher than 1400 cm$^{-1}$, indicating the absence of ketone and other functional groups.

$^{19}$F-NMR: −3 to −21 ppm 10F (CF$_3$, —CF$_2$—) −49 to −51 ppm 2F (—CF—)
The chemical shifts are relative to CF$_3$COOH.
Mass spectrum: 313 (M—F), 263 (M—CF$_3$)

Elemental analysis:
|   | Calcd. | Found |
|---|--------|-------|
| C: | 21.7% | 21.1% |
| F: | 68.7% | 67.9% |

The cyclic perfluoroketones of the invention are thermally and chemically very stable liquids and useful as reaction solvents in the chemical industry, heat transfer media in various applications, leak test fluids in the semiconductor industry, inert liquids for vapor phase soldering, dielectric fluids in electric equipment, and the like. They can be converted into more stable cyclic perfluoroethers and used as precursors to various compounds having a cyclic perfluoroether residue. The method of the invention can produce such cyclic perfluoroketones with ease.

Although some preferred embodiments have been described, many modifications and variations may be made thereto in the light of the above teachings. It is therefore to be understood that within the scope of the appended claims, the invention may be practiced otherwise than as specifically described.

We claim:

1. A cyclic perfluoroketone of the formula (1):

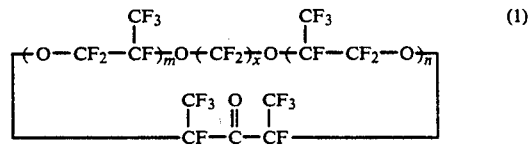

wherein x is an integer of from 2 to 10, and m and n are independently an integer of from 0 to 2.

2. A method for preparing a cyclic perfluoroketone as set forth in claim 1, comprising the step of reacting a perfluorodicarboxylic acid difluoride of the formula (2):

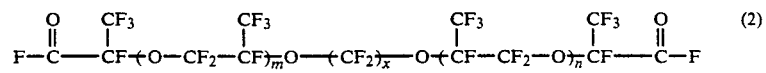

wherein x is an integer of from 2 to 10, and m and n are independently an integer of from 0 to 2 with a carbonate salt in an aprotic polar solvent.

3. The cyclic perfluoroketone of claim 1, wherein x is 2 and m and n are both 0.

4. The method of claim 2, wherein x is 2 and m and n are both 0.

5. The method of claim 2, wherein the carbonate salt is of the formula $M_2CO_3$ wherein M is Li, Na, K, Rb, Cs or Ag.

6. The method of claim 2, wherein the carbonate salt is $Na_2CO_3$ or $K_2CO_3$.

7. The method of claim 2, wherein the carbonate salt is anhydrous.

8. The method of claim 2, wherein the aprotic polar solvent is dimethylformamide, dimethylacetamide, hexamethylphosphoric triamide, diethyl ether, tetrahydrofuran, dioxane, ethylene glycol dimethyl ether, diethylene glycol dimethyl ether, triethylene glycol dimethyl ether, or tetraethylene glycol dimethyl ether.

9. The method of claim 2, wherein the carbonate and perfluorodicarboxylic acid difluoride are used in a molar ratio of from 1.2:1 to 5.0:1.

10. The method of claim 2, wherein the reaction is conducted at 20° to 200° C.

* * * * *